United States Patent [19]
Flaa et al.

[11] Patent Number: 6,165,981
[45] Date of Patent: *Dec. 26, 2000

[54] STABILIZING SOLUTIONS FOR PROTEINS AND PEPTIDES

[75] Inventors: Cathy Flaa, Norfolk, Va.; Alberto Sabucedo; Bruce Chin, both of Miami, Fla.; Roger Bauer, Ft. Lauderdale, Fla.

[73] Assignee: Dade Behring Inc., Deerfield, Ill.

[*] Notice: This patent is subject to a terminal disclaimer.

[21] Appl. No.: 08/400,158

[22] Filed: Mar. 7, 1995

[51] Int. Cl.$^7$ .............................. A61K 38/00; C07K 14/00
[52] U.S. Cl. .............................. 514/21; 514/12; 530/324; 530/350; 530/362; 530/363
[58] Field of Search .................. 514/21, 12; 530/324, 530/350, 362, 363

[56] References Cited

U.S. PATENT DOCUMENTS

| | | | |
|---|---|---|---|
| 4,931,385 | 6/1990 | Block et al. | 435/7.1 |
| 5,217,890 | 6/1993 | Dagget | 435/188 |

FOREIGN PATENT DOCUMENTS

| | | |
|---|---|---|
| 528 499 A1 | 2/1993 | European Pat. Off. . |
| 44 05 249 A1 | 8/1994 | Germany . |
| WO94/27156 | 11/1994 | WIPO . |

OTHER PUBLICATIONS

Diagnosis of Perioperative Myocardial Infarction with Measurement of cardiac Troponin I. Adams et al. New England Journal of Medicine 330: 670–674, Mar. 10, 1994.

Cardiac Troponin–T Immunoassay for Diagnosis of Acute Myocardial Infarction. Wu et al. Clin. Chem. 40/6, 900–907 (1994).

Troponin I Found Beneficial for Non–cardiac Surgery Patients. Kahn, J. Clin. Chem. News vol. 20, No. 5, May 1994.

Molecular cloning of human cardiac troponin I using polymerase chain reaction. FEBS 08842, vol. 270, No. 1,2 Sep. 1990.

Cardiac Troponin I. A Marker with High Specificity for Cardiac Injury. Adams et al. Circulation, vol. 88, No. 1, Jul. 1993.

Use of Cardiac Troponin I to Diagnose Perioperative Myocardial Infarction in Coronary Artery Bypass Grafting. Clin. Chem. 40/11, 2066–2070 (1994). Mair et al.

Myoglobin Fluormetric Enzyme Immunoassay, Baxter Diagnostics Inc.

CK–MB Fluorometric Enzyme Immunoassay. Baxter Diagnostic Inc.

Cardiac T™ Elisa Troponin T. Boehringer Mannheim Corp.

Elisa Troponin–T. Boehringer Mannheim Corp.

*Calbiochem Catalogue,* 1994–1995, Albumins, Bovine Serum; Selecting a BSA for Your Application. Fibroblast Growth Factor, Basic Human Recombinant . . . see composition of sterile filtered Solution. Creatitine Phosphokinase, see soluite it is provided in.

*Methods of Enzymatic Analysis,* vol. III:508–518, Ch. 7.4 Creatine Kinase (W. Gerhardt).

*Methods of Enzymology*—Guide to Protein Purification. 182:83–89, Maintaining Protein Stability, (Murray P. Deutscher).

*Primary Examiner*—Robert J. Hill, Jr.
*Assistant Examiner*—Abdel A. Mohamed
*Attorney, Agent, or Firm*—Cynthia Tymeson; Lois Ruszala

[57] ABSTRACT

Disclosed are compositions for stabilizing proteins and fragments of the proteins. The composition contains buffer, salt, reducing agents, chelating agents and stabilizing proteins. The composition may be used to prepare highly stable diagnostic calibrators or controls and is particularly useful for calibrators or controls for cardiac markers such as troponin.

18 Claims, 7 Drawing Sheets

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 210 amino acids
      (B) TYPE: amino acid
      (C) STRANDEDNESS: single
      (D) TOPOLOGY: linear (ii) MOLECULE TYPE: peptide (x) PUBLICATION INFORMATION:
      (A) AUTHORS: VALLINS, WILLIAM J.
         BRAND, NIGEL J.
         DABHADE, NINA
         BUTLER-BROWNE, GILLIAN
         YACOUB, MAGDI H.
         BARTON, PAUL J.R.
      (B) TITLE: MOLECULAR CLONING OF HUMAN CARDIAC TROPONIN I
         USING POLYMERASE CHAIN RECTION
      (C) JOURNAL: FEBS Lett.
      (D) VOLUME: 270
      (E) ISSUE: 1,2
      (F) PAGES: 57-61
      (G) DATE: SEPTEMBER-1990
      (K) RELEVANT RESIDUES IN SEQ ID NO:1: FROM 1 TO 212

(xi) SEQUENCE DESCRIPTION: SEQ ID NO:1:

```
Met Ala Asp Gly Ser Ser Asp Ala Ala Arg Glu Pro Arg Pro Ala Pro
1               5                   10                  15

Ala Pro Ile Arg Arg Arg Ser Ser Asn Tyr Arg Ala Tyr Ala Thr Glu
                20                  25                  30

Pro His Ala Lys Lys Lys Ser Lys Ile Ser Ala Ser Arg Lys Leu Gln
            35                  40                  45

Leu Lys Thr Leu Leu Leu Gln Ile Ala Lys Gln Glu Leu Glu Arg Glu
        50                  55                  60

Ala Glu Glu Arg Arg Gly Glu Lys Gly Arg Ala Leu Ser Thr Arg Cys
65                  70                  75                  80

Gln Pro Leu Glu Leu Ala Gly Leu Gly Phe Ala Glu Leu Gln Asp Leu
                85                  90                  95

Cys Arg Gln Leu His Ala Arg Val Asp Lys Val Asp Glu Glu Arg Tyr
                100                 105                 110

Asp Ile Glu Ala Lys Val Thr Lys Asn Ile Thr Glu Ile Ala Asp Leu
            115                 120                 125

Thr Gln Lys Ile Phe Asp Leu Arg Gly Lys Phe Lys Arg Pro Thr Leu
        130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
```

```
                    165                 170                 175
Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Lys Phe
        195                 200                 205

Glu Ser
    210

(2) INFORMATION FOR SEQ ID NO:2:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: peptide (x) PUBLICATION INFORMATION:
        (A) AUTHORS: VALLINS, WILLIAM J.
            BRAND, NIGEL J.
            DABHADE, NINA
            BUTLER-BROWNE, GILLIAN
            YACOUB, MAGDI H.
            BARTON, PAUL J.R.
        (B) TITLE: MOLECULAR CLONING OF HUMAN CARDIAC TROPONIN I
            USING POLYMERASE CHAIN RECTION
        (C) JOURNAL: FEBS Lett.
        (D) VOLUME: 270
        (E) ISSUE: 1,2
        (F) PAGES: 57-61
        (G) DATE: SEPTEMBER-1990
        (K) RELEVANT RESIDUES IN SEQ ID NO:2: FROM 1 TO 80

(xi) SEQUENCE DESCRIPTION: SEQ ID NO:2:

Ala Asp Gly Ser Ser Asp Ala Ala Arg Glu Pro Arg Pro Ala Pro Ala
1               5                   10                  15

Pro Ile Arg Arg Arg Ser Ser Asn Tyr Arg Ala Tyr Ala Thr Glu Pro
            20                  25                  30

His Ala Lys Lys Lys Ser Lys Ile Ser Ala Ser Arg Lys Leu Gln Leu
        35                  40                  45

Lys Thr Leu Leu Leu Gln Ile Ala Lys Gln Glu Leu Glu Arg Glu Ala
    50                  55                  60

Glu Glu Arg Arg Gly Glu Lys Gly Arg Ala Leu Ser Thr Arg Cys Gln
65                  70                  75                  80

(2) INFORMATION FOR SEQ ID NO:3:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Arg Ala Tyr Ala Thr Glu Pro His Ala Lys Lys Lys Ser Lys Ile Ser
1               5                   10                  15

Ala Ser Arg Lys Leu Gln Leu Thr Leu Leu Leu Gln Ile Ala Lys
            20                  25                  30

Gln Glu Leu
        35
```

STABILIZING SOLUTIONS FOR PROTEINS AND PEPTIDES

FIELD OF THE INVENTION

The present invention relates generally to aqueous solutions to stabilize proteins and peptides. In particular this invention relates to aqueous calibrator and control solutions for diagnostic assays for proteins and peptides, particularly: troponin, myoglobin, CK, CK isoenzymes, LD, LD isoenzymes and myosin, and fragments thereof and most particularly troponin and troponin fragments including synthetic and recombinant peptides of troponin.

BACKGROUND OF THE INVENTION

A number of physiological conditions and states are associated with increased levels of CK-MB, myoglobin, myosin and troponin. Elevated levels generally are associated with myocardial infarction and other conditions which result in myocardial injury.

Principally because of the association of increased levels of these proteins with acute myocardial infarction, tests for acute myocardial infarction (AMI) have been or are being devised to determine the level of these proteins in bodily fluids. Thus, these proteins have become known as cardiac markers.

Acute myocardial infarction continues to be a major cause of illness and death, particularly in the United States. An estimated 1.5 million admissions to hospitals can be attributed to suspected myocardial infarction or related cardiac disease. Of these patients, only roughly 25% are actually suffering an AMI while another 30% are admitted with unstable angina, 20% have stable coronary artery disease (CA), and the remaining 25% have no CAD. Differentiation of those patients who require immediate care and hospitalization from those who are not in danger is of great value in providing effective medical care, reducing hospitalization costs, and effectively managing hospital facilities. Current studies indicate that early intervention is critical for optimum therapeutic measures.

These therapeutic measures have the potential to restore blood flow to the damaged myocardium, limit the size of the infarct, and thus preserve cardiac function. New therapeutic intervention mechanisms, specifically thrombolytic agents such as streptokinase and tissue plasminogen activator are available to restore coronary artery blood flow and reduce the incidence of morbidity. Most clinicians believe that intervention must take place as soon as possible and should be well within the first four hours after the onset of chest pain.

Thus, an ideal cardiac marker or combination of markers should be cardiac tissue specific, it should be diagnostic within four hours after the onset of AMI, it should remain somewhat elevated for at least seven days after AMI but it should detect reinfarction even during the first few days of the first AMI.

Diagnosis of AMI is now based on an abnormal electrocardiogram (ECG), clinical symptoms and history, and elevated cardiac enzyme levels. Currently, CKMB is often used as the "definitive" serum marker for AMI.

However, often the ECG and clinical presentation give inconclusive or conflicting predictions of cardiac trauma. CK-MB testing has some limitations in contributing to final diagnosis. Skeletal muscle damage and strenuous exercise can artificially elevate CK-MB levels and confuse the clinical picture. In addition, CK-MB does not become diagnostically elevated until 4–6 hours after AMI. In addition, CK-MB levels become non-diagnostic 48–72 hours after AMI.

CK-MB has been prepared in a control solution to monitor diagnostic measurements of this analyte, however CK-MB is an enzyme which has limited stability in human serum and common buffered aqueous solutions. U.S. Pat. No. 4,994,375 discloses a stable reconstituted aqueous based control. Currently there are immunoassay kits, such as the DADE® STATUS® CK-MB Fluorometric Enzyme Immunoassay Kit available on the market for the determination of CK-MB levels. Many of these kits include calibrators. Control solutions containing CK-MB, such as the DADE® CK-MB/Myoglobin Immunoassay Control, are also commercially available.

Myoglobin is a marker present in both skeletal and cardiac muscle. Myoglobin levels are elevated within 2 hours of AMI. The serum level peaks in 6–8 hours but returns to non-diagnostic levels after 24–36 hours. However, serum myoglobin levels are also increased after skeletal muscle injury. There are a few immunoassay kits, such as the DADE® STRATUS® Myoglobin Fluorometric Enzyme Immunoassay Kit for the determination of myoglobin levels, that are commercially available. Myoglobin containing control solutions have been prepared and are commercially available from such sources as DADE® CK-MB/Myoglobin Immunoassay Control.

Troponin is a protein complex having a molecular weight of about 85 kD that performs the regulatory function of the contractile mechanism of the muscle tissue. The amino acid sequences of subunits which comprise the troponin complex has been determined. See, for instance, Vallins W. J. et al., *Molecular cloning of human cardiac troponin I using polymerase chain reaction,* FEBS LETTERS :Vol. 270, number 1, 2 Sep. 1990. Troponin is composed of three subunits of similar molecular weight, which, in the presence of calcium, cooperate to control either the contraction or relaxation of the muscle. The three subunits are designated troponin T, C, and I. Both the T and I molecules contained in heart muscle have amino acid sequences which are cardiac specific. Thus, both troponin T and troponin I have potential for superior specificity in testing for damage of myocardial origin. Damage to cardiac tissue causes these contractile proteins to be released into circulation fairly rapidly after injury providing the potential for sensitivity as well. Troponin is diagnostic 4–6 hours after AMI and remains elevated for 4–14 days.

Proteins of the contractile apparatus such as troponin are part of an insoluble protein complex. Thus, when purified troponin is placed in serum it is difficult to solubilize. In addition, purified preparations of troponin tend to be very labile and apparent changes in its conformation and/or adhesion to container surfaces tend to complicate quantification of the molecule. Thus, it is very difficult to design an aqueous solution which stabilizes troponin. Currently commercially available calibrators and controls used for diagnostic assays for troponin have very limited stability in liquid form.

Thus a need exists for aqueous solutions useful for solubilizing and stabilizing troponin. Such solutions can function as a diagnostic control or calibrator matrix for troponin and other cardiac markers or other proteins that are difficult to solubilize and/or stabilize. In addition, the matrix is useful for storing the protein(s).

Several criteria need to be met when formulating a calibrator or control base for troponin or other proteins that have stability or solubility issues similar to troponin. Stability issues are of primary concern. Liquid products are preferred for reproducibility and ease of use and should be stable. However if the product is lyophilized, it should be stable after reconstitution. Previous troponin calibrators are based on human serum derived products and contribute very little to the stability of the composition. For instance, the published "dating" of human serum based lyophilized troponin T calibrators and controls of the Boehringer Mannheim ELISA-TEST® Troponin T after reconstitution is only 6 hours at 2 to 8 C and 3 months when aliquoted and stored at −20 C. A matrix which increases the stability of the product is highly desirable.

Moreover, use of normal or processed human serum presents health issues to both clinicians and manufacturers. Thus, a matrix which lowers health risks is also highly desirable.

The calibrators in a synthetic matrix must mimic the shape of a response curve using normal human serum. This is important to ensure that results read off a standard curve generated with the matrix are accurate when comparing the results to the actual biological milieu.

In a diagnostic assay, non-specific binding of the analyte to the test surface (e.g. solid support such as test tubes, paper, slides etc.) must be minimized in order to keep calibration accurate and eliminate any risks of "discrepant" results. Thus, the non-specific binding of the analyte in a matrix must be minimized and must be similar to the non-specific binding of samples. It is also important that during storage, the protein or protein fragment does not appreciably bind to the storage container.

There are instances when an analyte analogue may be more desirable than the actual analyte. If an analyte analogue is used instead of the analyte, the binding of the analogue must mimic the binding of the analyte. Particular care must be used when selecting analogues for proteins because the immunobinding of the analogue must mimic that of the protein. Thus, any conformational dependence of the protein for the binding site must be maintained in the analogue. In addition, stability of the analogue should be the same or greater than that of the analyte. Again, the stability of the protein analyte may be related to its conformation. Finally, if an analogue is substituted for an analyte, it is desirable that the analogue be more readily available than the analyte.

SUMMARY OF THE INVENTION

This invention provides a stabilized clinical laboratory non-human serum derived control and/or calibrator matrix to be used in performing calibration curves for diagnostic assays and for monitoring the precision and accuracy of diagnostic assays for certain unstable and/or less soluble proteins such as cardiac markers. In particular, the stabilized matrix is useful for solubilizing and/or stabilizing troponin I, troponin T, CK-MB, myoglobin, myosin and fragments of these proteins or analytes.

The matrix uses a novel mixture of constituents to impart a stability to the analyte that is at least equivalent and preferably better than the stability of the analyte in normal human serum. In particular, an aqueous based mixture of a buffer, albumin, gelatin, chelating agent, reducing agent and salts, all at a slightly acidic to mildly alkaline pH is used to stabilize and solubilize the analyte or analyte analogue.

Also disclosed are methods to prepare the matrix.

DETAILED DESCRIPTION OF THE INVENTION

Figure 1:
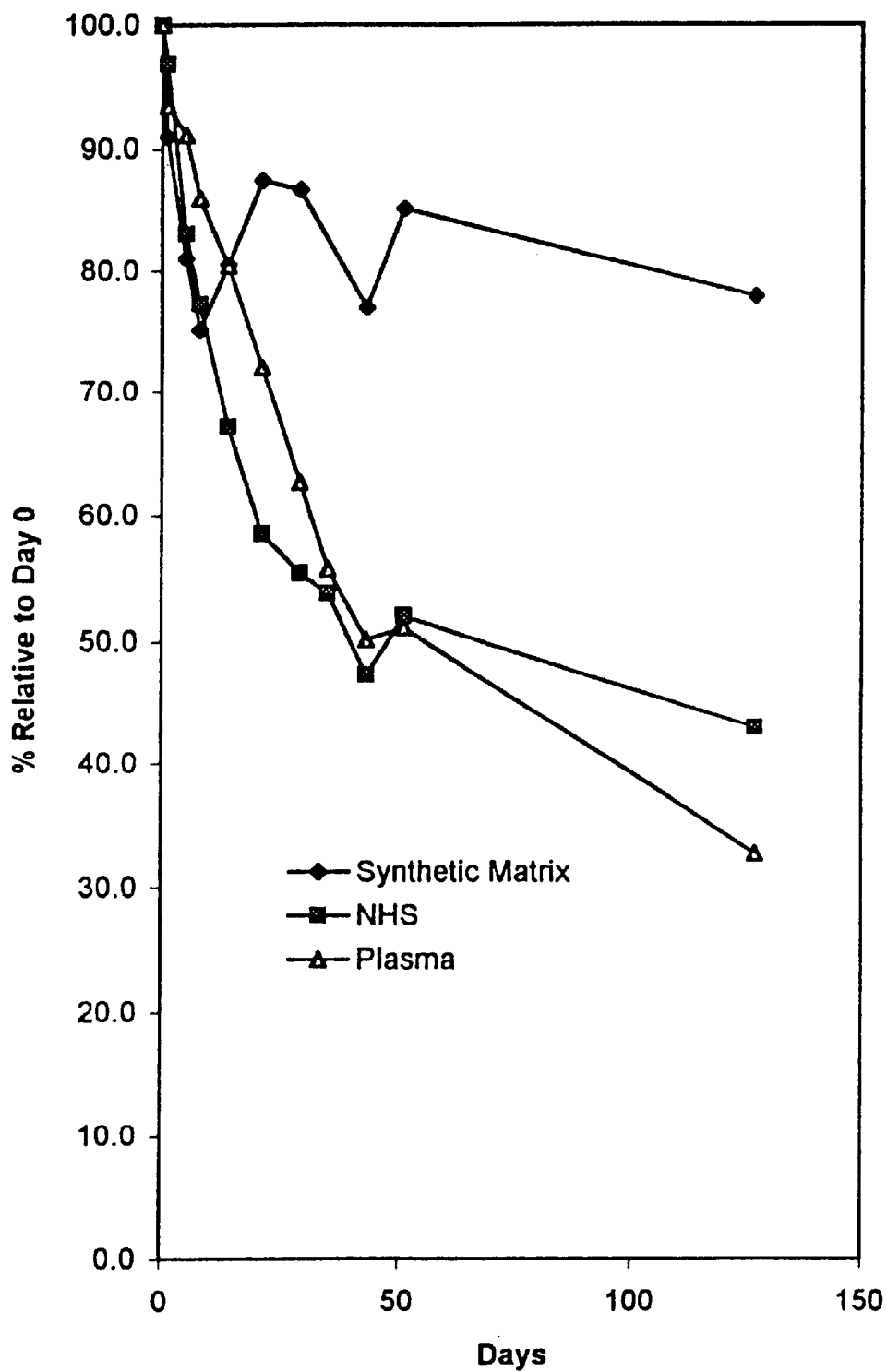
FIG. 1 shows a comparison of the stability at 2–8 C of recombinant full length troponin I in various matrices.

The stabilized clinical laboratory non-human serum derived control and/or calibrator matrix for cardiac markers and other unstable proteins comprises an aqueous solution of a buffer, a stabilizing protein such as albumin, ovalbumin, casein and the like, a chelating agent, a reducing agent and a salt, all at a slightly acidic to mildly alkaline pH.

The matrix can contain a blocking agent such as gelatin, detergents and protease inhibitors. A preservative may be added to prevent microbial growth. An analyte or analyte analogue such as cardiac markers or other unstable or relatively insoluble proteins or fragments thereof are also added. If the calibrator or control will be lyophilized or frozen, sugars or other bulking agents are added.

The preferred buffers include buffers such as TRIS buffers and phosphate buffers. Other buffers include: 3-(N-Morpholino) propane sulfonic acid (MOPS), N-Tris-hydroxymethyl methyl-2-aminoethane sulfonic acid (TES), 3-[N-bis (hydroxyethyl)-amino]-2-hydroxypropane sulfonic acid (DIPSO), Piperazine-N, N'Bis(2)-hydroxypropane sulfonic acid (HEPPSO), Tris-(hydroxymethyl) aminoethane, N-2-Hydroxyehtylpiperazine-N'-2-aminoethane sulfonic acid (HEPES), 3-[N-(Tris-hydroxymethyl) methylamino] -2-hydroxypropane sulfonic acid (TAPSO), and (2 p[2-Amino-2-oxoethyl) - amino] ethanesulfonic acid (ACES). The most preferred buffer is a phosphate such as sodium phosphate.

The concentration of the buffer may be from about 10 mM to 200 mM. Preferably the concentration is about 25 mM to 100 mM. Most preferably the concentration is about 50 mM.

The stabilizing protein may be albumin, ovalbumin, casein or the like. The stabilizing protein, as with the other ingredients, should be essentially free of contaminants that interfere with the stability of the analyte in the matrix. Substances that may destabilize or destroy protein structure such as proteases are examples of such contaminants. Albumin is a preferred stabilizing protein. The source of the albumin is not critical. The albumin may be native or recombinant in origin. The most available source of native albumin is of bovine origin. It is most preferred that the albumin be essentially protease-free if the protein analyte or analogue is susceptible to protease degradation. Alternatively, protease inhibitors can be added. The preferred concentration of albumin is from 5–20%, 8–12% and most preferably at about 10%.

Although not wishing to be bound by any particular theory, it is believed that the protein stabilizer functions to provide a protective effect to the analyte or analyte analogue.

A blocking agent (i.e. an agent to minimize the non specific binding of the analyte or analyte analogue to surfaces) such as gelatin, casein, ovalbumin and the like may be added. Gelatin is the preferred blocking agent. The gelatin, if of bovine origin, is added at a concentration of about 0.01 to 0.15%, most preferably 0.1%. If the gelatin is of a different origin (e.g. fish) the concentration is adjusted appropriately.

A chelating agent is also added. The preferred chelating agents are ethylenebis (oxyethylene nitrilio)tetraacetic acid (EGTA) and ethylene diamine tetracetic acid (EDTA), sodium citrate, or oxalate salts such as sodium, potassium, ammonnium or lithium oxalte. The most preferred chelating agent is EDTA. The concentration of chelating agents may be from 1 mM to 15 mM and most preferably is from 5 to 10 mM.

The preferred reducing agent is N-acetyl-cysteine (NAC). Examples of other reducing agents which may be used include 2-aminoethanethiol, 2-mercaptoethanol, 2-mercaptoethylanine and dithiothreitol.

The concentration of reducing agent may be from about 0 to 5 mM, preferably the reducing agent is about 2 mM to 3.5 mM, and most preferably about 2.6 mM.

The pH may be from about 5.0 to 8.0. Slightly acidic pH values lower the non-specific binding of the troponin. The preferred range of pH is about 5 to 7.5 and most preferably about 7.0.

The preferred salt is sodium chloride. Many other salts may be substituted. Examples of other salts include potassium salts, ammonium salts, and lithium salts.

If a protease inhibitor is added, aprotinin and "Protease Inhibitor" (Sigma) are effective and may be used at the manufacturer's recommended concentration. Examples of other protease inhibitors include (2S, 3R)-3-Amino-2-hydroxy-5-methylhexanoyl]-Val-Val-Asp (Amastatin-Sigma), [2S,3R]-3-Amino-2-hydroxy-4-[4-nitrophenyl]-butanoyl-L-leucine, Antipain, [2S,3R]-3-Amino-2-hydroxy-5-methylhexanoyl]-Val-Val-Asp (Epiamastatin-Sigma), ([2R,3R]-3-Amino-2-hydroxy-4-phenylbutanoyl)-L-leucine (Epibestatin-Sigma), Foroxymithine, Acetyl-Leu-Leu-Arg-al (Leupeptin-Sigma), 4-Amino-3-hydroxy-6-methyl-heptanoic acid, 4-Amino-3-hydroxy-6-methylheptanoic acid, N-($\alpha$-Rhamnopyranosyloxy-hydroxyphosphinyl)-Leu-Trp and phenyl methane sulfonyl fluoride (PMSF).

The preferred detergents, if added, are SDS and Triton X-100. Other detergents include Tween-20, Brij, Sorbitin, Tergital and Nonidet. The concentration of detergents may be from 0.05% to 0.3%. The preferred range is from about 0.05% and 0.2%. The most preferred concentration is 0.1%.

The preservative may be added to prevent microbial and fungal growth. The preservatives may be clotrimazole of at least 0.03%, chloramphenicol of at least 0.017%, or sodium azide of at least 0.05%. Other preservatives include gentamicin, mycostatin, thimerasol and Kathon at an effective concentration.

To prepare the matrix, plastics such as polypropylene should be used. This minimizes loss of proteins to glass due to non specific binding to glass. Alternatively, glass based labware can be utilized but should be siliconized prior to use.

If the calibrator or control matrix is to be lyophilized or frozen, bulking agents are added. The preferred bulking agents are trehalose at 3 to 10% and sucrose at about 100 mM. The most preferred concentration of trehalose is about 5–10%. Other bulking agents include glucose, sucrose, galactose, manose, maltose, lactose, isomaltose, cellobiose, mannobiose, melbiose, maltotriose, nystose, maltotetraose, maltopentaose, maltohexaose, and maltoheptaose.

One liter of the matrix may be prepared by dissolving about 30 grams of BSA, about one gram of gelatin, about 15 grams of sodium chloride, 3 grams of EDTA, about 50 grams of trehalose, a preservative and a clinically appropriate level of the analyte or analyte analogue in 700 ml of 0.50 mM sodium phosphate buffer. After all ingredients are dissolved the pH is adjusted to 7.0 and then a sufficient volume of a buffer, such as sodium phosphate, is added to bring the volume to 1.0 L. The solution is sterile filled in suitable containers and lyophilized. The lyophilized analyte containing matrix is reconstituted by adding one liter of a diluent containing 65 grams of BSA, 25 grams of NaCl, protease inhibitor, and about 0.4 grams of NAC.

Alternatively, one liter of the matrix may be prepared by dissolving about 100 grams of BSA, about one gram of gelatin, about 40 grams of sodium chloride, 3 grams of EDTA, a preservative, and 0.4 grams of NAC and a clinically appropriate level of the analyte or analyte analogue in 700 ml of 0.50 m sodium phosphate. After all ingredients are dissolved the pH is adjusted to 7.0 and then a sufficient volume of a buffer, such as sodium phosphate is added to bring the volume to 1.0 L. The liquid may be aliquoted and stored refrigerated or frozen. If the liquid is to be frozen, bulking agents are also added.

Surprisingly for the troponin I analyte, troponin I fragments also have increased stability. This is surprising because the stability of the troponin I fragments was found to be less than that of the full length troponin I when the matrix is normal human serum. In addition, certain troponin I fragments had similar binding to the anti-troponin antibody used in the assay when compared with the full length troponin I molecule.

Thus, the present invention has many advantages over the prior art. The matrix is non-human serum derived which prevents the user (and manufacturing personnel) from exposure to many of the diseases which can be spread by contact with human blood products. The matrix is also able to keep the analyte stable in liquid form for an extended period of time. Current formulations can also be lyophilized or frozen and can be reliably reconstituted or thawed for up to at least nine months shelf storage with very little variation in calibration. After reconstitution or thawing, the analyte is stable for up to three weeks at 2–8C. Spiking of the analyte into the matrix yields a calibration curve which closely parallels a human serum curve. Non-specific binding levels in the "synthetic" matrix also closely parallel the levels seen in normal human serum. Moreover, fragments such as recombinantly or synthetically produced peptide fragments of proteins can be utilized instead of full length proteins. Indeed these fragments are preferred because of their stability in the matrix coupled with the availability and reproducibility of the recombinantly or synthetically produced fragments. The analyte analogue (e.g. the fragment) should have binding characteristics similar to that of the full length marker. Methods to determine and map epitope sites are known to those skilled in the art as is the art of producing antibodies against a specific antigen.

It is to be understood that the matrix of the present invention can be used for many analytes but it is particularly useful when the analyte is an unstable and/or relatively insoluble protein such as the cardiac markers, in particular troponin and CK-MB.

EXAMPLE 1

Preparation of a Calibrator/Control Matrix

To about seven hundred milliliters of purified water was added with stirring about three grams of EDTA (stirred until dissolved), then about 40.0 grams of sodium chloride, about 6.9 grams of sodium phosphate, monobasic, about 0.424 mgs of NAC, about 50 grams of trehalose, about 3.3 milliliters of a stock solution of chloramphenicol to provide a final concentration of 165 mg/mL, about 0.75 milliliters of a stock solution of clortrimazole to provide a final concentration of 3 ppms, about 10 milliliters of a 1% aqueous solution of gelatin, then stirring slowly, about 95 grams of protease free bovine serum albumin until dissolved), and 2 milliliters of a 25% solution of sodium azide. The pH was adjusted to 7.3 and the total volume was adjusted to 1 liter with purified water. The final matrix may be sterile filtered.

EXAMPLE 2

Preparation of a Lyophilized Calibrator/Control Matrix

To about seven hundred milliliters of purified water is added about three grams of EDTA, about 15 grams of sodium chloride, about 7 grams of sodium phosphate, monobasic, about 50 grams of trehalose, about 3.3 milliliters of a stock solution of chloramphenicol to provide a final concentration of 165 mg/mL, about 0.75 milliliters of a stock solution of clortrimazole to provide a final concentration of 3 ppms, about 10 milliliters of a 1% aqueous solution of gelatin, and about 30 grams of bovine serum albumin. The pH is adjusted to 5.5 and the total volume is adjusted to 1 liter with purified water. The final matrix is sterile filtered and lyophilized. A reconstitution diluent of one liter is prepared by combining in aqueous solution about 65 grams of albumin, 25 grams of sodium chloride and 0.4 grams of NAC, protease inhibitor and about 2 milliliters of a 25% solution of sodium azide.

EXAMPLE 3

Preparation of a Calibrator/Control Matrix

To about seven hundred milliliters of purified water is added about five grams of EDTA, about 50 grams of sodium chloride, about 7 grams of sodium phosphate, monobasic, about 0.4 mgs of NAC, about 3.3 milliliters of a stock solution of chloramphenicol to provide a final concentration of 165 mg/mL, about 0.75 milliliters of a stock solution of clortrimazole to provide a final concentration of 3 ppms, about 10 milliliters of a I% aqueous solution of gelatin, and about 95 grams of protease free bovine serum albumin. The pH is adjusted to 6.5 and the total volume is adjusted to 1 liter with purified water. The final matrix may be sterile filtered.

EXAMPLE 4

Preparation of Calibrators using a recombinant protein

A stock solution of human recombinant troponin I was prepared in polypropylene labware by adding a sufficient amount of recombinant troponin I so that calibrators or controls can be made that have concentrations ranging from about 0 to 100 ng/mL of troponin I.

In one experiment solutions of troponin I were prepared by adding a sufficient amount of an unpurified solution of recombinant troponin I at 100 ug/mL to the following matrices:

Normal human serum, plasma, and a matrix similar to that described in Example 1. For each matrix the final volume was 15 milliliters of a 100 ng/mL solution of recombinant troponin I. The recombinant troponin I had the following sequence:

Met Ala Asp Gly Ser Ser Asp Ala Ala Arg Glu Pro Arg Pro
Ala Pro Ala Pro Ile Arg Arg Arg Ser Ser Asn Tyr Arg
Ala Tyr Ala Thr Glu Pro His Ala Lys Lys Lys Ser Lys
Ile Ser Ala Ser Arg Lys Leu Gln Leu Lys Thr Leu Leu
Leu Gln Ile Ala Lys Gln Glu Leu Glu Arg Glu Ala Glu
Glu Arg Arg Gly Glu Lys Gly Arg Ala Leu Ser Thr Arg
Cys Gln Pro Leu Glu Leu Ala Gly Leu Gly Phe Ala Glu
Leu Gln Asp Leu Cys Arg Gln Leu His Ala Arg Val Asp
Lys Val Asp Glu Glu Arg Tyr Asp Ile Glu Ala Lys Val
Thr Lys Asn Ile Thr Glu Ile Ala Asp Leu Thr Gln Lys
Ile Phe Asp Leu Arg Gly Lys Phe Lys Arg Pro Thr Leu
Arg Arg Val Arg Ile Ser Ala Asp Ala Met Met Gln Ala
Leu Leu Gly Ala Arg Ala Lys Glu Ser Leu Asp Leu Arg
Ala His Leu Lys Gln Val Lys Lys Glu Asp Thr Glu Lys
Glu Asn Arg Glu Val Gly Asp Trp Arg Lys Asn Ile Asp
Ala Leu Ser Gly Met Glu Gly Arg Lys Lys Lys Phe Glu
Ser and included a 6 His carboxy terminus tail and a seven amino acid sequence from the phage T7 Gene 10 leader sequence at the amino terminus. See, also Vallins W. J. et al., *Molecular cloning of human cardiac troponin I using polymerase chain reaction*, FEBS LETTERS :Vol. 270, number 1, 2 Sep. 1990.

Aliquots of each of the three troponin I solutions were stored at 2–8 C and evaluated for stability. On each day of the evaluation an aliquot of each troponin I solution was analyzed on a Stratus II Fluorometric Analyzer. The Stratus II Fluorometric Analyzer is sold by Dade International Inc. For principles of operation of the analyzer and immunoassay see for instance U.S. Pat. No. 4,517,288 incorporated herein by reference and Giegle et al. *Clinical Chemistry* 28:1894–1898 (1982). The analyzer measures the rate of change of a fluorescent signal. Generally, an antibody to an analyte, such as troponin I, is pre-immobilized on a solid phase of glass fiber filter paper. For troponin I, an aliquot of each troponin I solution is applied to the antibody and immunologically binds to the antibody to form a reaction zone. Next, a conjugate of alkaline phosphatase-antitroponin I antibody is added to the reaction zone. The conjugate binds to the troponin I. A substrate wash solution containing 4 methyl umbelliferyl phosphate is applied to the reaction zone. A front surface fluorometer measures the rate of change of fluorescence in rate units designated as millivolts per minute (mvm).

The results of the evaluation can be seen in FIG. 1. As can be seen from FIG. 1, the matrix of the present invention provided more stability to the troponin-I analyte than normal human serum or plasma.

EXAMPLE 5

Preparation of Calibrators using a recombinantly produced peptide

A stock solution of human recombinant troponin I peptide is prepared in polypropylene labware by adding a sufficient amount of a recombinant troponin I peptide so that calibrators or controls can be made that have concentrations ranging from about 0 to 100 ng/mL of troponin I.

In one experiment solutions of troponin I were prepared by adding a sufficient amount of a recombinant 80 amino acid peptide of recombinant troponin I having the sequence Ala Asp Gly Ser Ser Asp Ala Ala Arg Glu Pro Arg Pro Ala
Pro Ala Pro Ile Arg Arg Arg Ser Ser Asn Tyr Arg Ala
Tyr Ala Thr Glu Pro His Ala Lys Lys Lys Ser Lys Ile
Ser Ala Ser Arg Lys Leu Gln Leu Lys Thr Leu Leu Leu
Gln Ile Ala Lys Gln Glu Leu Glu Arg Glu Ala Glu Glu
Arg Arg Gly Glu Lys Gly Arg Ala Leu Ser Thr Arg Cys
Gln also having a six histidine tail at the carboxy terminus and seven amino acids from the phage T7 Gene 10 leader sequence at the amino terminus (see, also Vallins W. J. et al., *Molecular cloning of human cardiac troponin I using polymerase chain reaction,* FEBS LETTERS :Vol. 270, number 1, 2 Sep. 1990) at 7500 ng/mL to the following matrices:

Normal human serum, processed human plasma, plasma, and a matrix similar to that described in Example 1 to provide a 100 ng/mL solution of recombinant troponin I peptide in each matrix.

Aliquots of each of the four troponin I solutions were stored at 2–8 C and evaluated for stability. On each day of the evaluation an aliquot of each troponin I solution was analyzed on a Stratus II Fluorometric Analyzer. The Stratus II Fluorometric Analyzer is sold by Dade International Inc. For principles of operation of the analyzer and immunoassay see for instance U.S. Pat. No. 4,517,288 incorporated herein by reference and Giegle et al. *Clinical Chemistry* 28:1894–1898 (1982). The analyzer measures the rate of change of a fluorescent signal. Generally, an antibody to an analyte, such as troponin I, is pre-immobilized on a solid phase of glass fiber filter paper. For troponin I, an aliquot of each troponin I solution is applied to the antibody and immunologically binds to the antibody to form a reaction zone. Next, a conjugate of alkaline phosphatase-anti-troponin I antibody is added to the reaction zone. The conjugate binds to the troponin I. A substrate wash solution containing 4 methyl umbelliferyl phosphate is applied to the reaction zone. A front surface fluorometer measures the rate of change of fluorescence in rate units designated as millivolts per minute (mvm).

Figure 2:
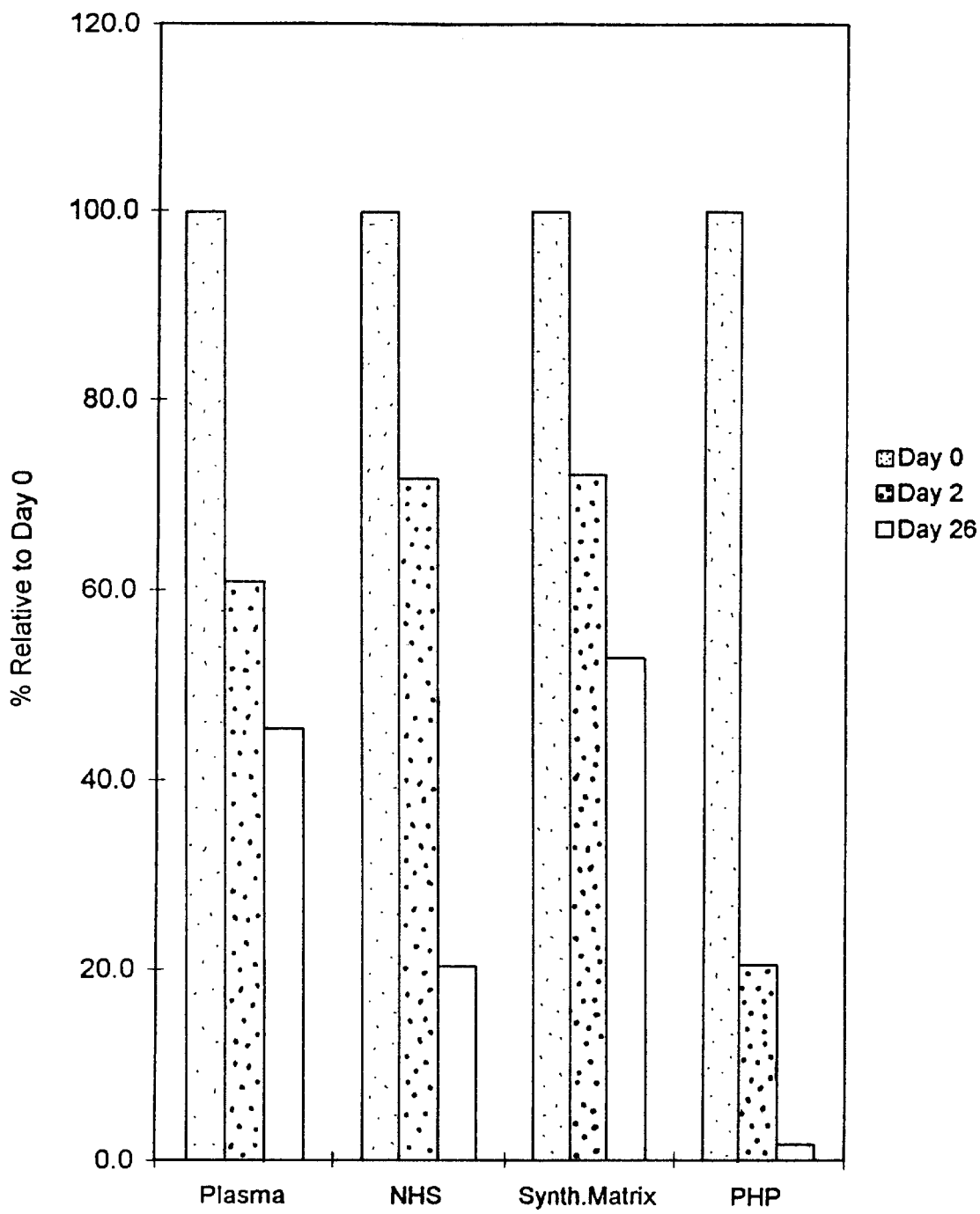
FIG. 2 shows a comparison of the stability at 2–8 C of a recombinantly produced 80 amino acid peptide in various matrices.

The results of the evaluation can be seen in FIG. 2. As can be seen from FIG. 2, the matrix of the present invention provided more stability to the troponin-I analyte than normal human serum, processed human plasma (PHP) or plasma.

EXAMPLE 6

Preparation of Calibrators using a synthetic peptide

A stock solution of a synthetic peptide of troponin I is prepared in polypropylene labware by adding a sufficient amount of the peptide so that calibrators or controls can be made that have concentrations ranging from about 0 to 50 ng/mL of troponin I.

In one experiment solutions of troponin I were prepared by adding a sufficient amount of a synthetic peptide of troponin I having the sequence Arg Ala Tyr Ala Thr Glu Pro His Ala Lys Lys Lys Ser Lys
Ile Ser Ala Ser Arg Lys Leu Gln Leu Lys Thr Leu Leu
Leu Gln Ile Ala Lys Gln Glu Leu at a stock concentration (in purified water) of 1.4 mg/mL to the following matrices:

Normal human serum, plasma, processed human plasma, a synthetic matrix at pH 7.6 containing 100 mM Tris, 150 mM NaCl, 0.1% Gelatin, 2% BSA, 0.1% Sodium Azide, and 0.1% Zonyl fluorosurfactant (DXMC)and a matrix similar to that described in Example 1 to provide 50 ng/mL solution of troponin I in each matrix and a 10 ng/mL solution of troponin I.

Aliquots of each of the four troponin I solutions were stored at 2–8 C and evaluated for stability. On each day of the evaluation an aliquot of each troponin I solution was analyzed on a Stratus II Fluorometric Analyzer. The Stratus II Fluorometric Analyzer is sold by Dade International Inc. For principles of operation of the analyzer and immunoassay see for instance U.S. Pat. No. 4,517,288 incorporated herein by reference and Giegle et al. *Clinical Chemistry* 28:1894–1898 (1982). The analyzer measures the rate of change of a fluorescent signal. Generally, an antibody to an analyte, such as troponin I, is pre-immobilized on a solid phase of glass fiber filter paper. For troponin I, an aliquot of each troponin I solution is applied to the antibody and immunologically binds to the antibody to form a reaction zone. Next, a conjugate of alkaline phosphatase-anti-troponin I antibody is added to the reaction zone. The conjugate binds to the troponin I. A substrate wash solution containing 4 methyl umbelliferyl phosphate is applied to the reaction zone. A front surface fluorometer measures the rate of change of fluorescence.

Figure 3:
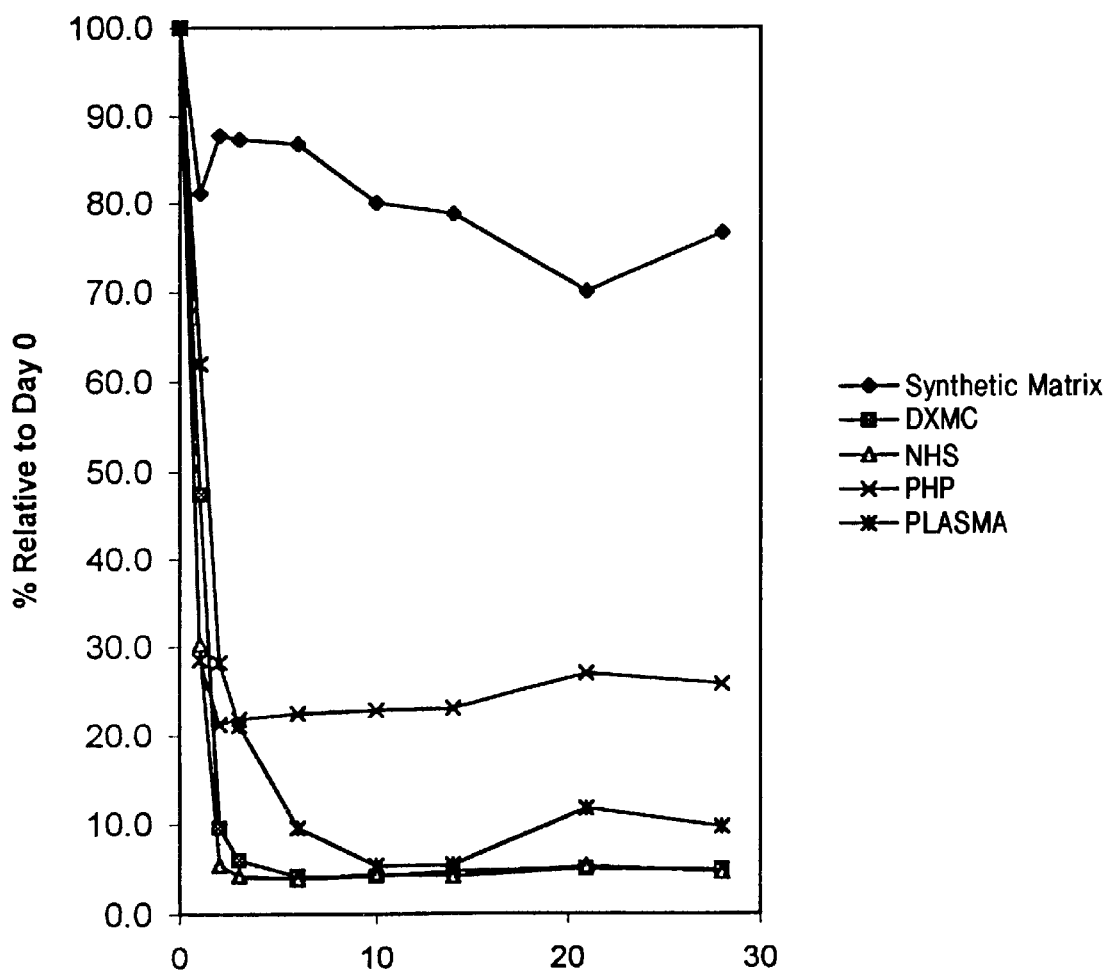
FIG. 3 shows a comparison of the stability at 2–8 C of a 10 ng/mL calibrator of a synthetic peptide of troponin I in various matrices.
Figure 4:
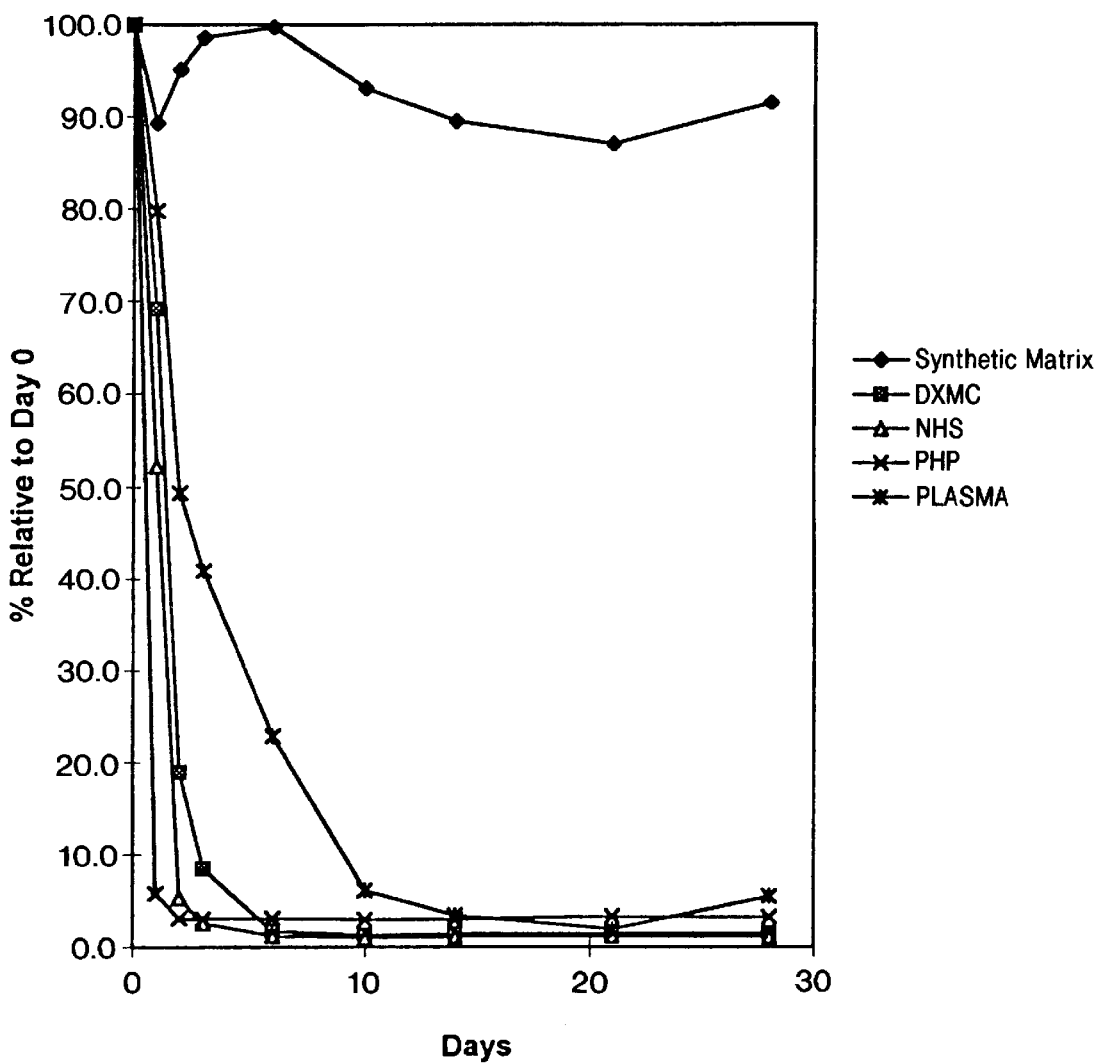
FIG. 4 shows a comparison of the stability at 2–8 C of a 50 ng/mL calibrator of a synthetic peptide of troponin I in various matrices.

The results of the evaluation can be seen in FIGS. 3 and 4. As can be seen from FIGS. 3 and 4, the matrix of the present invention provided more stability to the troponin-I analyte analogue than normal human serum, processed human plasma (PHP), the synthetic base DXMC, or plasma.

EXAMPLE 7

Preparation of Calibrators using a synthetic peptide

A stock solution of a synthetic peptide of troponin I is prepared in polypropylene labware by adding a sufficient amount of the peptide so that calibrators or controls can be made that have concentrations ranging from about 0 to 100 ng/mL of troponin I.

In one experiment solutions of 40 ug/mL troponin I were prepared by adding a sufficient amount of a synthetic peptide of troponin I having the sequence Arg Ala Tyr Ala Thr Glu Pro His Ala Lys Lys Lys Ser Lys
Ile Ser Ala Ser Arg Lys Leu Gln Leu Lys Thr Leu Leu
Leu Gln Ile Ala Lys Gln Glu Leu to the following matrices:

Normal human serum, plasma, and a matrix similar to that described in Example 1 (except that the pH of the synthetic matrix was adjusted to 5.5) to provide 3.0 milliliters of a 100 ng/mL solution of troponin I in each matrix. In addition, EDTA was added to each matrix at about 3.5 mg/mL.

A second set of solutions was prepared as above, except that the solutions also contained a protease inhibitor cocktail of PEPSTATIN at 680 ng/mL and aminoethylbenzenesulfonyl fluoride at 208 ug/mL.

Aliquots of each of the six troponin I solution were stored at 37 C and evaluated for stability. On each day of the evaluation an aliquot of each troponin I solution was analyzed on a Stratus II Fluorometric Analyzer. The Stratus II Fluorometric Analyzer is sold by Dade International Inc. For principles of operation of the analyzer and immunoassay see for instance U.S. Pat. No. 4,517,288 incorporated herein by reference and Giegle et al. *Clinical Chemistry* 28:1894–1898 (1982). The analyzer measures the rate of change of a fluorescent signal. Generally, an antibody to an analyte, such as troponin I, is pre-immobilized on a solid phase of glass fiber filter paper. For troponin I, an aliquot of each troponin I solution is applied to the antibody and immunologically binds to the antibody to form a reaction zone. Next, a conjugate of alkaline phosphatase-anti-troponin I antibody is added to the reaction zone. The conjugate binds to the troponin I. A substrate wash solution containing 4 methyl umbelliferyl phosphate is applied to the reaction zone. A front surface fluorometer measures the rate of change of fluorescence in rate units designated as millivolts per minute (mvm).

Figure 5:
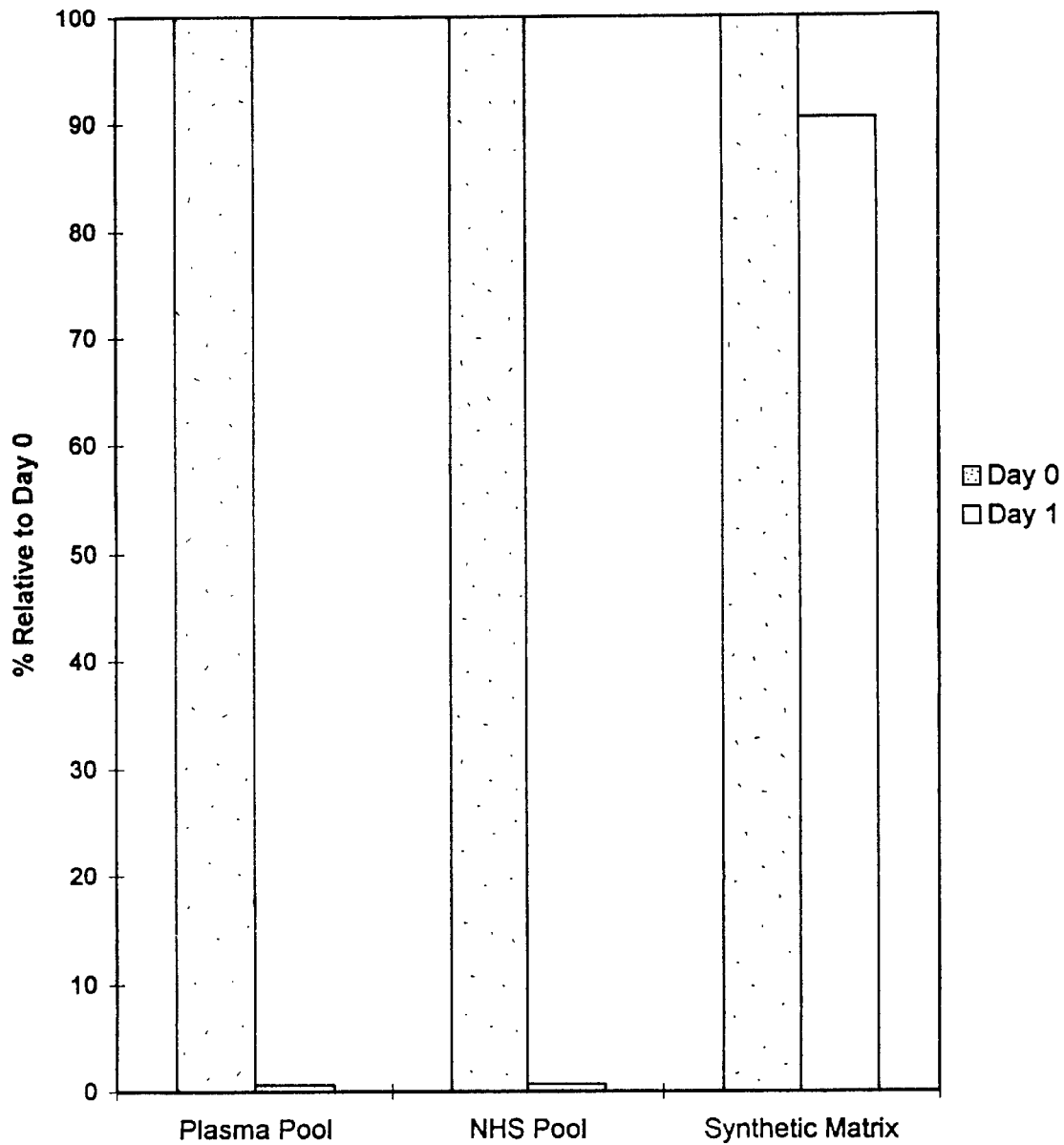
FIG. 5 shows a comparison of the stability at 37 C of a synthetic peptide of troponin I in various matrices.
Figure 6:
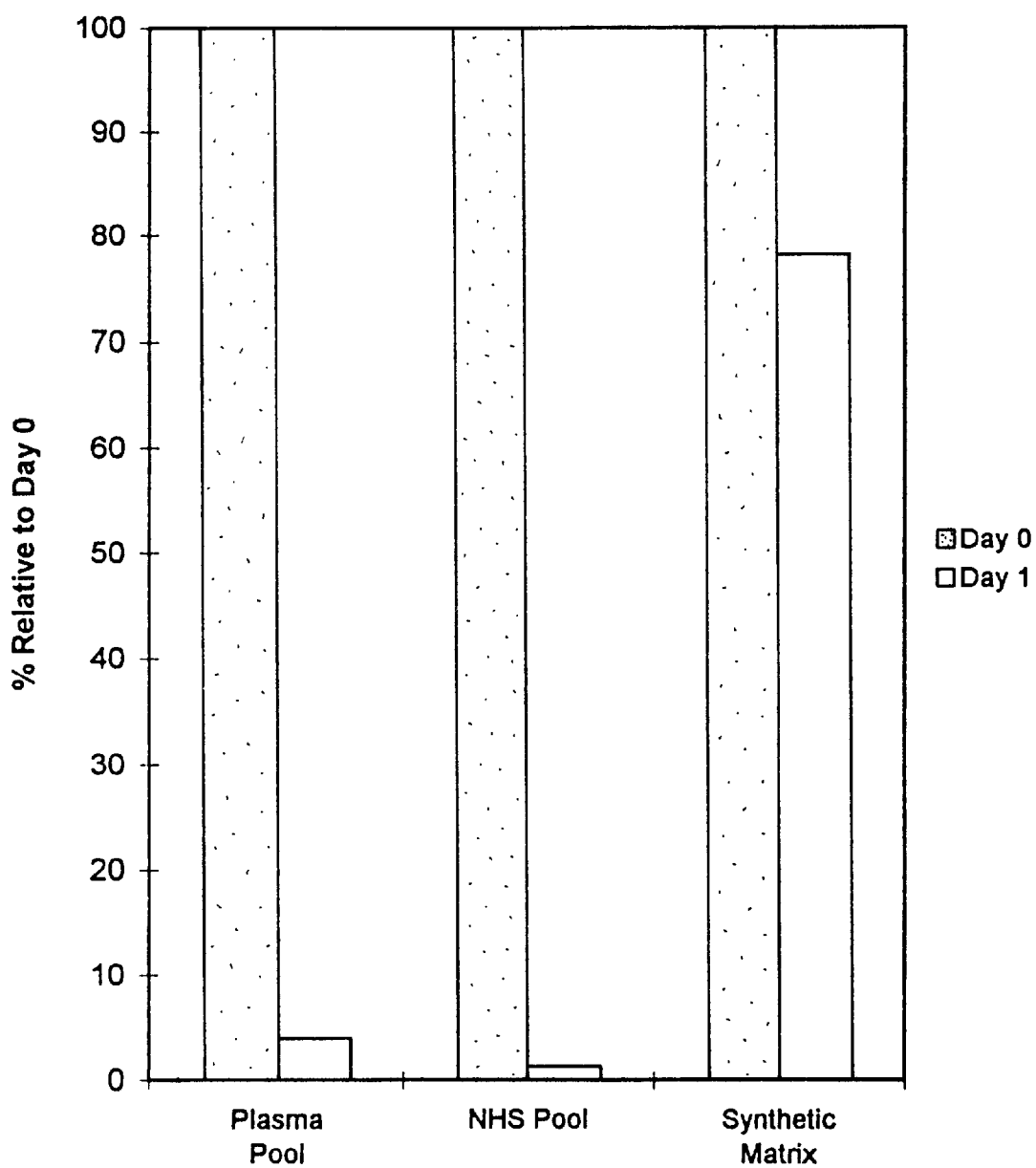
FIG. 6 shows a comparison of the stability at 37 C of a synthetic peptide of troponin I in various matrices where all of the matrices include a protease inhibitor.
Figure 7:
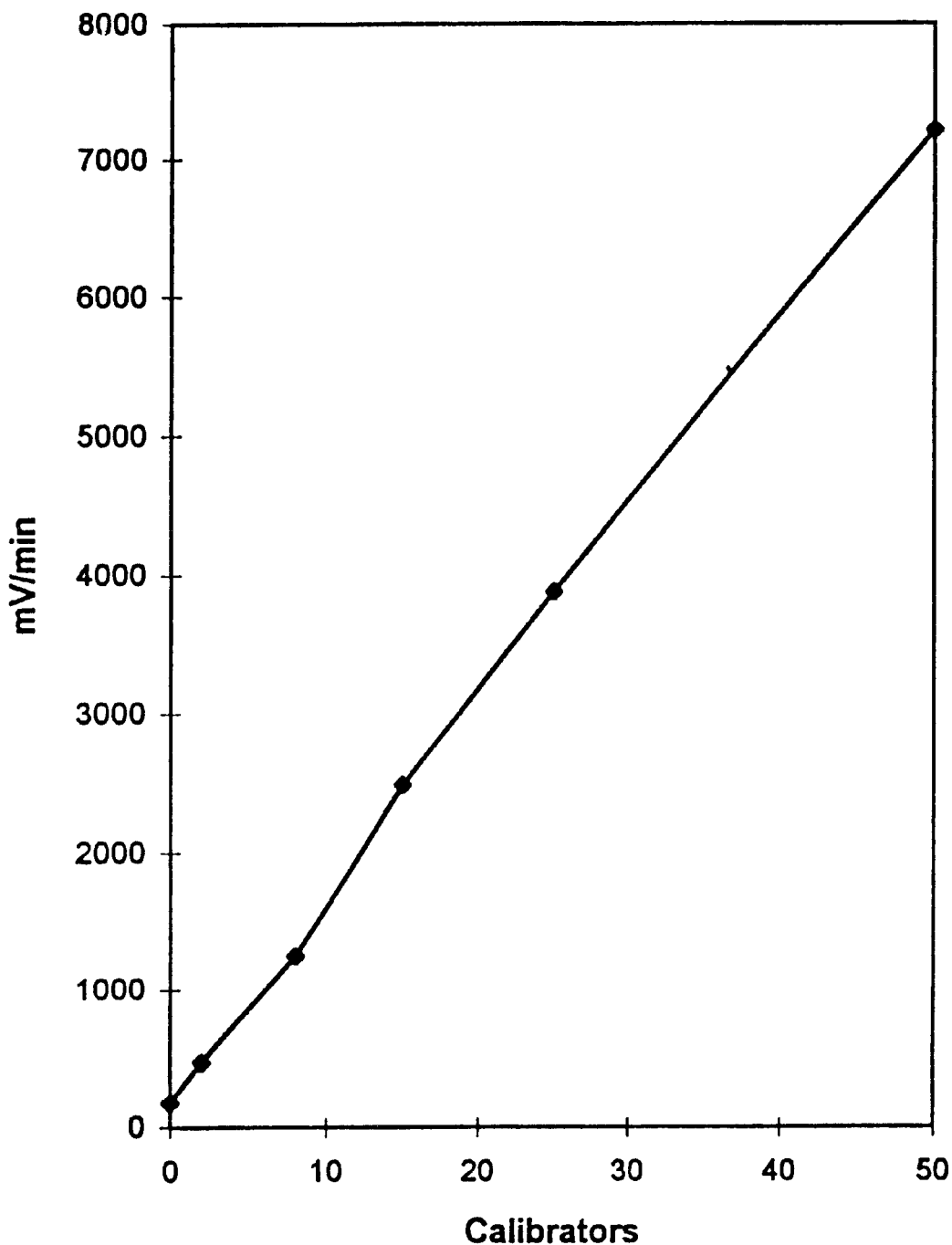
FIG. 7 shows a calibration curve of different levels of a synthetic peptide of troponin I in a matrix of the present invention.

The results of the evaluation can be seen corresponding to FIGS. 5 and 6. As can be seen from FIGS. 5 and 6, the matrix of the present invention provided more stability to the troponin-I analyte analogue than normal human serum, or plasma with or without the protease inhibitors.

EXAMPLE 8

Performing an Immunoassay using Troponin I Calibrators and Controls

A stock solution of a synthetic peptide of troponin I is prepared in polypropylene labware by adding a sufficient amount of the peptide so that calibrators or controls can be made that have concentrations ranging from about 0 to 50 ng/mL of troponin I.

In one experiment solutions of troponin I were prepared by adding a sufficient amount of a synthetic peptide of troponin I having the sequence Arg Ala Tyr Ala Thr Glu Pro His Ala Lys Lys Lys Ser Lys Ile Ser Ala Ser Arg Lys Leu Gln Leu Lys Thr Leu Leu Leu Gln Ile Ala Lys Gln Glu Leu at a stock concentration of 1.4 mg/mL to a matrix similar to that described in Example 1 to provide calibrator solutions of troponin I having the following concentrations: 0 ng/mL, 2 ng/mL, 8 ng/mL, 15 ng/mL, 25 ng/mL and 50 ng/mL. Controls were prepared in a similar fashion to provide control solutions at about 4 ng/mL, 20 ng/mL and 35 ng/mL.

Aliquots of each of the troponin I solutions were stored frozen. Frozen solutions were thawed and a calibration curve was generated. The controls prepared as discussed above and controls prepared from normal human serum were also evaluated. The range for the normal human serum controls was 2.1–2.9 ng/mL for the low control and 15.9–21.5 for the high control. Duplicate samples of each troponin I solution was analyzed on a Stratus II Fluorometric Analyzer and a calibration curve was generated. The Stratus II Fluorometric Analyzer is sold by Dade International Inc. For principles of operation of the analyzer and immunoassay see for instance U.S. Pat. No. 4,517,288 incorporated herein by reference and Giegle et al. *Clinical Chemistry* 28:1894–1898 (1982). The analyzer measures the rate of change of a fluorescent signal. An antibody to an analyte, such as troponin I, is pre-immobilized on a solid phase of glass fiber filter paper. An aliquot of each troponin I solution is applied to the antibody and immunologically binds to the antibody to form a reaction zone. Next, a conjugate of alkaline phosphatase-anti-troponin I antibody is added to the reaction zone. The conjugate binds to the troponin I. A substrate wash solution containing 4 methyl umbelliferyl phosphate is applied to the reaction zone. A front surface fluorometer measures the rate of change of fluorescence in rate units designated as millivolts per minute (mvm).

The results of the calibration in millivolts per minute (mvm) can be seen in Table 1 and the calibration curve is presented graphically in FIG. 6.

TABLE 1

| Calibrator Level | Rate 1 (mvm) | Rate 2 (mvm) | Mean (mvm) |
|---|---|---|---|
| 0 | 171.5 | 180.4 | 176.0 |
| 2 | 463.7 | 464.5 | 464.1 |
| 8 | 1287.5 | 1208.5 | 1248.0 |
| 15 | 2487.6 | 2481.9 | 2484.8 |
| 25 | 3926.6 | 3826.6 | 3876.6 |
| 50 | 7668.0 | 6767.0 | 7217.5 |

Control recoveries are presented in Table 2.

TABLE 2

| Control | Rep. 1 (ng/mL) | Rep. 2 (ng/mL) | Rep. 3 (ng/mL) | Rep. 4 (ng/mL) | Mean (ng/mL) |
|---|---|---|---|---|---|
| Syn. Low | 3.7 | 3.6 | | | 3.7 |
| Syn. Mid | 17.1 | 16.3 | | | 16.7 |
| Syn. Hi | 32.6 | 32.8 | | | 32.7 |
| Serum Lo | 2.6 | 2.5 | 2.5 | 2.3 | 2.5 |
| Serum Hi | 18.2 | 18.7 | 19.7 | 18.0 | 18.7 |

EXAMPLE 9

Preparing CK-MB Calibrators/Controls

A stock solution of CK-MB is prepared by adding a sufficient amount of the CK-MB so that calibrators or controls can be made that have concentrations ranging from about 0 to 125 ng/mL of CK-MB.

Solutions of CK-MB are prepared by adding a sufficient amount of CK-MB to a matrix similar to that described in Example 1 to provide calibrator solutions of CK-MB having the following concentrations: 0, 4, 10, 25, 60 and 125 ng/mL. Controls are prepared in a similar fashion

EXAMPLE 10

Preparing Troponin T Calibrators/Controls

A stock solution of Troponin T is prepared by adding a sufficient amount of the Troponin T so that calibrators or controls can be made that have concentrations ranging from about 0 to 12 ng/mL of Troponin T.

Solutions of Troponin T are prepared by adding a sufficient amount of Troponin T to a matrix similar to that described in Example 1 to provide calibrator solutions of Troponin T having the following concentrations: 0, 1, 2, 4, 8, and 12 ng/mL. Controls are prepared in a similar fashion

EXAMPLE 11

Stability of Calibrators at 4C

A study was conducted to determine the stability of calibrators prepared similarly to the calibrators prepared in Example 6. Immunoassay kits, which included calibrators, were prepared and stored at about 4 C and evaluated on a Stratus II Fluorometric Analyzer. On each day of the evaluation calibration curves were generated using unopened vials of calibrators and controls and a patient pool to determine if the controls and patient pool (both stored at −70 C and freshly thawed prior to use) recovered within the expected ranges. The ranges of the controls and patient pool had been previously established by obtaining at least 80 replicates of each control level and patient pool. The control limits were set at ±2 standard deviations or 15% of the mean, whichever was larger. All of the assay components, thus the calibrators, were determined to be acceptable if the duplicates of each control and patient pool were within 12% of and if the mean of the duplicates fell within the calculated range. The assay kit, thus the calibrators, were found to be acceptable for at least 60 days. A second study conducted similarly confirmed the results.

EXAMPLE 12

Stability of Calibrators at 25C

Two studies were conducted similarly to that described in Example 11, except that the kit reagents were stored at 25C instead of 4C. The kits, thus the calibrators, were found to be stable for at least about 7–14 days.

EXAMPLE 13

Stability of Calibrators at 2 to 8C/−70 C

A study was conducted similarly to that described in Example 11, except that the calibrators at 2 ng/mL and 25 ng/mL were also stored at −70C. The recovery of the frozen calibrators was determined and compared to calibrators stored at 4C. A ratio of the 2–8 C/−70 C was determined. The calibrators at −70 C, were found to be stable for at least 60 days. A second study conducted similarly confirmed the results.

In another study, the recovery of a patient pool (stored and used as described above in Example 11 with an established recovery range also as described above in Example 11) against a calibration curve generated from calibrators stored at −70 C was determined. The calibrators were found to be stable for at least 100 days.

---

We claim:

1. A liquid composition for stabilizing proteins and protein fragments or analytes comprising:
   a. a buffer;
   b. a reducing agent;
   c. a stabilizing protein;
   d. a chelating agent;
   e. a salt; and
   f. troponin or a fragment thereof.

2. The composition of claim 1 wherein the troponin fragment is SEQ ID NO: 3.

3. The composition of claim 1 wherein the troponin fragment is SEQ ID NO: 2.

4. The composition of claim 1 wherein the composition is frozen.

5. The composition of claim 1 further comprising a blocking agent.

6. The composition of claim 5 wherein the blocking agent is gelatin.

7. The composition of claim 1 wherein the protein stabilizer is an albumin.

8. The composition of claim 7 wherein the albumin is protease free.

9. The composition of claim 1 further comprising a bulking agent.

10. The composition of claim 9 wherein the composition is lyophilized.

11. The composition of claim 9 wherein the bulking agent is selected from the group consisting of trehalose, glucose, sucrose, galactose, manose, maltose, lactose, isomaltose, cellbiose, mannobiose, melbiose, maltotriose, nytose, maltotetrose, maltopentose, maltohexose, and maltoheptose.

12. A composition for stabilizing proteins and protein fragments or analytes comprising:
   a. a buffer;
   b. a reducing agent selected from the group consisting of N-acetyl-cysteine, 2-aminoethanethiol, 2-mercaptoethanol, 2-mercaptoethylanine and dithiothreitol;
   c. a stabilizing protein selected from the group consisting of albumin, ovalbumin and casein;
   d. a chelating agent selected from the group consisting of ethylenebis (oxyethylene nitrilio)-tetraacetic acid (EGTA), ethylene diamine tetraacetic acid (EDTA), citrates, or oxalates;
   e. a salt; and
   f. troponin or a fragment thereof.

13. The composition of claim 12 wherein the composition is frozen.

14. The composition of claim 12 further comprising a blocking agent.

15. The composition of claim 14 wherein the blocking agent is gelatin.

16. The composition of claim 12 further comprising a bulking agent.

17. The composition of claim 16 wherein the composition is lyophilized.

18. The composition of claim 16 wherein the bulking agent is selected from the group consisting of trehalose, glucose, sucrose, galactose, manose, maltose, lactose, isomaltose, cellbiose, mannobiose, melbiose, maltotriose, nytose, maltotetrose, maltopentose, maltohexose, and maltoheptose.

* * * * *